United States Patent

Scartazzini et al.

[11] Patent Number: 5,421,870
[45] Date of Patent: Jun. 6, 1995

[54] CONCENTRATED AQUEOUS LIQUID FORMULATIONS OF COLOR FORMERS

[75] Inventors: Roger Scartazzini, Giebenach, Switzerland; Klaus Huber, Freiburg, Germany

[73] Assignee: Ciba-Geigy Corporation, Ardsley, N.Y.

[21] Appl. No.: 126,819

[22] Filed: Sep. 24, 1993

[30] Foreign Application Priority Data

Sep. 30, 1992 [CH] Switzerland ............... 3047/92

[51] Int. Cl.⁶ .................................. C09D 11/00
[52] U.S. Cl. ......................... 106/21 R; 106/21 A; 106/21 C
[58] Field of Search ............... 106/21 R, 21 A, 21 C

[56] References Cited

U.S. PATENT DOCUMENTS

| | | | |
|---|---|---|---|
| 3,681,390 | 8/1972 | Lin | 260/335 |
| 3,746,562 | 7/1973 | Lin | 117/36.2 |
| 4,363,664 | 12/1982 | Delaney | 106/21 R |
| 4,444,591 | 4/1984 | Kawai et al. | 106/21 R |
| 4,536,220 | 8/1985 | Kondo et al. | 106/21 R |
| 4,687,862 | 8/1987 | Obitsu et al. | 106/21 R |
| 4,973,712 | 11/1990 | Zink | 549/265 |
| 5,066,814 | 11/1991 | Zink | 548/407 |
| 5,071,480 | 12/1991 | Zink | 106/21 R |
| 5,178,670 | 1/1993 | Klug et al. | 106/21 R |

FOREIGN PATENT DOCUMENTS

| | | |
|---|---|---|
| 266311 | 5/1988 | European Pat. Off. . |
| 331636 | 9/1989 | European Pat. Off. . |
| 333649 | 9/1989 | European Pat. Off. . |
| 384895 | 8/1990 | European Pat. Off. . |
| 561738 | 9/1993 | European Pat. Off. . |
| 567077 | 9/1975 | Switzerland . |

*Primary Examiner*—Helene Klemanski
*Attorney, Agent, or Firm*—George R. Dohmann

[57] ABSTRACT

The invention relates to concentrated aqueous liquid formulations of color formers comprising
(a) as color former one or more fluorans of formula (1),
(b) as anionic surfactants
(ba) sulfated alkanes
(bb) alkanesulfonates
(bc) sulfonated carboxylates or
(bd) sulfated carboxylates, and
(be) acid esters or salts thereof of polyadducts of alkylene oxides, and
(c) a thickener.

The formulations are used in heat-sensitive recording materials.

27 Claims, No Drawings

CONCENTRATED AQUEOUS LIQUID FORMULATIONS OF COLOR FORMERS

The present invention relates to concentrated aqueous liquid formulations of colour formers, to a process for the preparation of said formulations and to the use thereof in heat-sensitive recording materials.

Concentrated aqueous liquid formulations of colour formers for heat-sensitive recording materials are known in the art, inter alia from U.S. Pat. No. 4,363,664. Such formulations are aqueous dispersions of a colour former and a surfactant. Surprisingly, it has now been found that liquid formulations which, in addition to containing one or more than one colour former and certain anionic surfactants, also contain a thickener, have excellent storage stability.

Accordingly, the invention relates to a liquid formulation comprising a) as colour former, a fluoran of formula

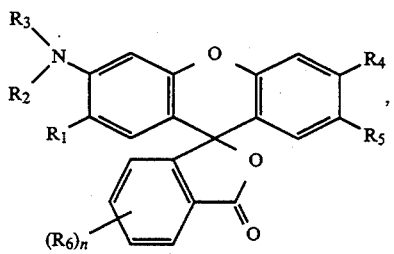

wherein $R_1$ is hydrogen or $C_1$–$C_4$alkyl;

$R_2$ and $R_3$ are each independently of the other hydrogen; $C_1$–$C_{12}$alkyl; unsubstituted or $C_1$–$C_4$alkyl- or halogen-substituted $C_4$–$C_7$cycloalkyl; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or $R_2$ and $R_3$ together with the linking nitrogen atom are an unsubstituted or $C_1$–$C_4$alkyl-substituted pyrrolidino, piperidino, morpholino, thiomorpholino or piperazino ring;

$R_4$ is hydrogen, hydroxy or $C_1$–$C_4$alkyl;

is nitro; $SO_2R_7$; $SO_2OR_8$; $SO_2NR_9R_{10}$; $COR_{11}$; $CONR_9R_{10}$; $C_1$–$C_4$haloalkl; $C_6$–$C_{10}$aryl which is unsubstituted or substituted by halogen, $C_1$–$C_4$alkyl, $C_1$–$C_4$haloalkyl, $C_1$–$C_4$alkoxy; phenylamino; phenyl-$C_1$–$C_4$alkylamino; phenyl-$C_1$–$C_4$alkyl; an unsubstituted or a halogen- or hydroxy-substituted 2-triazinyl or 1-benzotriazolyl radical;

$R_6$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_{11}$;

n is 0; 1; 2; 3; or 4;

$R_7$ is $C_1$–$C_8$alkyl; or $C_1$–$C_8$haloalkyl; unsubstituted phenyl or phenyl-$C_1$–$C_4$alkyl or phenyl or phenyl-$C_1$–$C_4$alkyl which are substituted by halogen, $C_1$–$C_4$alkyl, $C_1$–$C_4$haloalkyl or $C_1C_4$alkoxy;

$R_8$ is hydrogen, $C_1$–$C_8$alkyl; $C_1$–$C_8$haloalkyl; unsubstituted phenyl or phenyl-$C_1$–$C_4$alkyl or phenyl or phenyl-$C_1$–$C_4$alkyl which are substituted by halogen, $C_1$–$C_4$alkyl, $C_1$–$C_4$haloalkyl, $C_1$–$C_4$alkoxy;

$R_9$ and $R_{10}$ are each independently of the other hydrogen; or $C_1$–$C_8$alkyl; or $R_9$ and $R_{10}$, together with the linking nitrogen atom, are an unsubstituted or a $C_1$–$C_4$alkyl-substituted pyrrolidino, piperidino, morpholino, thiomorpholino or piperazino ring; and $R_{11}$ is hydrogen; hydroxy; $C_1$–$C_8$alkyl; $C_1$–$C_8$alkoxy; $C_1$–$C_8$haloalkyl; unsubstituted phenyl or phenyl which is substituted by halogen, $C_1$–$C_4$alkyl, $C_1$–$C_4$haloalkyl, or $C_1$–$C_4$alkoxy; phenyl-$C_1$–$C_4$alkyl or phenyl-$C_1$–$C_4$alkoxy;

(b) as anionic surfactants
(ba) sulfated alkanes
(bb) alkanesulfonates
(bc) sulfonated carboxylates
(bd) sulfated carboxylates, or
(be) acid esters or salts thereof of polyadducts of alkylene oxides, and (c) a thickener.

The novel formulation may contain components (a), (b) and (c) as single compounds or as a mixture of several compounds.

In the literature the individual substituent positions at the fluoran ring are numbered differently. In this specification, the following numbering has been adopted:

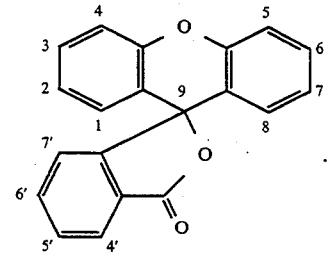

Within the scope of the above definition, the respective substituents or radicals have the following preferred meanings:

Halogen is fluoro, chloro or bromo, preferably fluoro or chloro.

Alkyl within the scope of each definition is straight-chain or branched alkyl. Examplary alkyl groups are methyl, ethyl, n-propyl, isopropyl, n-butyl, 1-methylbutyl, sec-butyl, tert-butyl, n-pentyl, amyl, isoamyl, n-hexyl, 2-ethylhexyl, n-heptyl, n-octyl, isooctyl, 1,1,3,3-tetramethylbutyl.

Haloalkyl will preferably represent $C_1$–$C_2$haloalkyl radicals such as trichloromethyl, trifluoromethyl, dichlorofluoromethyl, difluorochloromethyl, perchloroethyl, 1,1,2,2-tetrachloroethyl, 1,1,2,2-tetrafluoroethyl, 2,2,2-trichloroethyl. $R_5$ as $C_1$–$C_8$haloalkyl is preferably haloalkyl as defined above and also comprises alkyl radicals in which all or at least most of the C—H bonds are replaced by C—Cl or C—F.

Alkoxy is preferably methoxy, ethoxy, n-propoxy, isopropoxy, n-butoxy, isobutoxy, sec-butoxy and tert-butoxy. $C_1$–$C_4$Alkoxy-$C_1$–$C_4$alkyl is preferably methoxymethyl, methoxyethyl, ethoxymethyl or ethoxyethyl. Mono-$C_1$–$C_5$alkylamino is preferably methylamino, ethylamino, propylamino, butylamino and pentylamino. Di-$C_1$–$C_5$alkylamino comprises both the mixed as well as the corresponding substituted radicals such as methylethylamino, dimethylamino, diethylamino, methylpropylamino, methylbutylamino, di-n- propylamino, diisopropylamino, di-n-butylamino and di-n-pentylamino and the like.

In phenyl-$C_1$-$C_4$ alkyl and phenyl-$C_1$-$C_4$alkoxy, the phenyl moiety can be bound through a straight-chain or branched alkyl or alkoxy chain. Phenethyl, benzyl and phenylmethoxy are preferred.

The phenyl moiety of phenyl-$C_1$-$C_4$alkyl, phenyl-$C_1$-$C_4$alkoxy and phenyl itself is preferably unsubstituted or carries up to three identical or different substituents from among those cited.

$C_3$-$C_5$Alkenyl is typically allyl, 1-propenyl or 2-pentenyl, isopropenyl or 2-butenyl. Allyl is preferred. $C_4$-$C_7$Cyclohexyl is cyclobutyl, cyclopentyl, cyclohexyl or cycloheptyl. Cyclohexyl is preferred.

$C_6$-$C_{10}$Aryl is phenyl or naphthyl.

Preferred colour formers systems are those comprising as mixture components at least one fluoran of formula I, wherein $R_1$ is hydrogen or $C_1$-$C_4$alkyl;

$R_2$ and $R_3$ are each independently of the other hydrogen; $C_1$-$C_5$alkyl; or $R_2$ and $R_3$, together with the linking nitrogen atom, are an unsubstituted or $C_1$-$C_4$alkyl-substituted pyrrolidino or piperidino ring;

$R_4$ is hydrogen or $C_1$-$C_4$alkyl;

$R_5$ is nitro; $SO_2R_7$; $SO_2OR_8$; $SO_2NR_9R_{10}$; $COR_{11}$; $CONR_9R_{10}$; $C_1$-$C_4$haloalkyl; unsubstituted phenyl or phenyl which is substituted by halogen, $C_1$-$C_4$alkyl, $C_1$-$C_4$haloalkyl or $C_1$-$C_4$alkoxy; phenylamino; or phenyl-$C_1$-$C_4$alkylamino;

n is 0; 1; 2; 3; or 4;

$R_6$ if n is 1, 2, 3, or 4, is halogen; if n is 1 or 2, is $C_1$-$C_4$alkyl, $C_1$-$C_4$haloalkyl; or, if n is 1, is nitro, $COR_{11}$, amino, mono-$C_1$-$C_4$alkylamino or di-$C_1$-$C_4$alkylamino;

$R_7$ is $C_1$-$C_4$alkyl; or $C_1$-$C_4$haloalkyl; unsubstituted phenyl or phenyl-$C_1$-$C_2$alkyl or phenyl or phenyl-$C_1$-$C_2$alkyl which are substituted by halogen, $C_1$-$C_4$alkyl, $C_1$-$C_4$haloalkyl or $C_1$-$C_4$alkoxy;

$R_8$ is hydrogen, $C_1$-$C_4$alkyl; $C_1$-$C_4$haloalkyl; unsubstituted phenyl or phenyl-$C_1$-$C_2$alkyl or phenyl or phenyl-$C_1$-$C_2$alkyl which are substituted by halogen, $C_1$-$C_4$alkyl, $C_1$-$C_4$haloalkyl, $C_1$-$C_4$alkoxy;

$R_9$ and $R_{10}$ are each independently of the other hydrogen; or $C_1$-$C_8$alkyl; or $R_9$ and $R_{10}$, together with the linking nitrogen atom, are an unsubstituted or a $C_1$-$C_4$alkyl-substituted pyrrolidino or piperidino ring; and $R_{11}$ is hydrogen; $C_1$-$C_4$alkyl; $C_1$-$C_4$haloalkyl; $C_1$-$C_4$alkoxy; unsubstituted phenyl or phenyl which is substituted by halogen, $C_1$-$C_4$alkyl, $C_1$-$C_4$haloalkyl, or $C_1$-$C_4$alkoxy; or is phenyl-$C_1$-$C_2$alkyl or phenyl-$C_1$-$C_2$alkoxy, Preferred colour formers of formula (1) are those wherein $R_1$ is hydrogen or methyl;

$R_2$ and $R_3$ are each independently of the other hydrogen; $C_1$-$C_5$alkyl; or $R_2$ and $R_3$, together with the linking nitrogen atom, are an unsubstituted pyrrolidino or piperidino ring;

$R_4$ is hydrogen or methyl;

$R_5$ is nitro; $SO_2R_7$; $SO_2NR_9R_{10}$; $COR_{11}$; $CONR_9R_{10}$; $C_1$-$C_4$haloalkyl; unsubstituted phenyl or phenyl which is substituted by halogen, $C_1$-$C_4$alkyl, $C_1$-$C_4$haloalkyl, $C_1$-$C_4$alkoxy; or is phenyl-$C_1$-$C_4$alkyl; phenylamino; or phenyl-$C_1$-$C_4$alkylamino;

n is 0, 1, 2, 3, or 4;

$R_6$ if n is 1, 2, 3, or 4, is halogen; if n is 1 or 2, is methyl; or, if n is 1, is nitro, amino, mono-$C_1$-$C_4$alkylamino or di-$C_1$-$C_4$alkylamino;

$R_7$ is $C_1$-$C_4$alkyl; or $C_1$-$C_4$haloalkyl; unsubstituted phenyl or or phenyl which is substituted by halogen, $C_1$-$C_4$alkyl, or $C_1$-$C_4$alkoxy;

$R_9$ and $R_{10}$ are each independently of the other hydrogen; or $C_1$-$C_4$alkyl;

$R_{11}$ is hydrogen; $C_1$-$C_4$alkyl; $C_1$-$C_4$alkoxy; unsubstituted phenyl or phenyl which is substituted by halogen, $C_1$-$C_4$alkyl, $C_1$-$C_4$haloalkyl, or $C_1$-$C_4$alkoxy; or is phenyl-$C_1$-$C_2$alkyl or phenyl-$C_1$-$C_2$alkoxy.

The invention relates in particular to liquid formulations which comprise the colour formers of formula (1), wherein $R_5$ is $SO_2R_7$, $SO_2OR_8$, $SO_2NR_9R_{10}$, $COR_{11}$, $CONR_9R_{10}$, $C_1C_4$haloalkyl or nitro.

Among the compounds of formula (1) above, those compounds are preferred in which $R_5$ is $COR_{11}$ and, most particularly, those compounds in which $R_{11}$ is $C_1$-$C_4$alkyl, $C_1$-$C_4$alkoxy or phenyl-$C_1$-$C_4$alkoxy. Those compounds in which $R_{11}$ is $C_1$-$C_4$alkoxy or phenyl-$C_1$-$C_4$alkoxy are of preeminent interest.

Most preferably, component (a) is a colour former of formula (1), wherein $R_2$ and $R_3$ are each independently of the other $C_1$-$C_8$alkyl, $C_5$-$C_7$cycloalkyl, benzyl or allyl.

Among these compounds, particularly interesting compounds of formula (1) are those wherein $R_2$ and $R_3$ are each independently of the other $C_1$-$C_4$alkyl.

Further very important colour formers of formula (1) are those compounds wherein $R_5$ is phenyl; phenylamino; or phenyl-$C_1$-$C_4$alkylamino.

Component (ba) is a salt of fatty alcohol sulfates of formula

$$R_{12}-O-SO_3M_1, \qquad (2)$$

wherein $R_{12}$ is an alkyl radical of 6 to 18 carbon atoms, and $M_1$ is alkali metal.

The alkyl radical $R_{12}$ in this formula is branched or unbranched and is typically derived from hexanol, heptanol as well as from octyl, nonyl, decyl and dodecyl alcohol, and also from lauryl, myristyl, cetyl and stearyl alcohol.

$M_1$ is lithium, potassium or sodium. Potassium and sodium are preferred.

Preferred salts are the sodium salts of fatty alcohol sulfates of 6 to 12, preferably 8 or 9, carbon atoms. Especially good results are obtained with the sulfated branched isomers of the above mentioned alcohols, conveniently 2-ethylhexanol, trimethylhexanol and trimethylnonyl alcohol. The salts of the sulfate esters may be used alone or in admixture with one another in the novel formulation. Component (bb) may suitably be selected from those compounds in which the alkyl chain contains 8 to 20 carbon atoms. Preferred compounds of this type are the secondary alkanesulfonates (paraffin sulfonates) having an alkyl chain length of 14 to 18 carbon atoms, in which the alkyl chain contains the sulfonate group in random distribution.

The compounds suitable as component (bc) are sulfonates of esters of polycarboxylic acids such as malonic or succinic acid. Suitable compounds are diesters, typically dioctyl sulfosuccinates or monoesters such as monosulfosuccinates derived from $C_{12}$-$C_{24}$fatty alcohols or ethoxylated alkanolamides. Exemplary of such compounds are dihexyl sulfosuccinates, di-2-ethylhexyl sulfosuccinates, dioctyl sulfosuccinates or sulfosuccinamides. Particularly suitable are compounds of formula

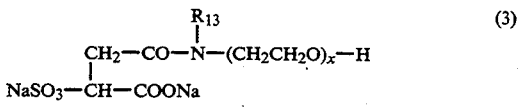

wherein $R_{13}$ is hydrogen or $(CH_2CH_2O)_xH$ and x is 1 to 10.

The compounds suitable as component (bd) are alkali metal salts, ammonium salts or amine salts of sulfated esters of fatty acids of 10 to 22 carbon atoms, typically the salts of lauric, myristic, palmitic or stearic acid or rosin salts. The potassium salt of a sulfated ester of a $C_2$-$C_{18}$fatty acid is especially preferred.

Acid esters or salts thereof of polyadducts of alkylene oxide (be) are suitably compounds of formula

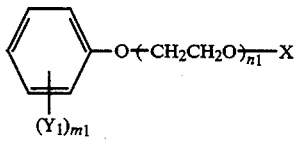

wherein $Y_1$ is $C_4$-$C_{12}$alkyl, phenyl, tolyl, phenyl-$C_1$-$C_3$alkyl or tolyl-$C_1$-$C_3$alkyl, $X_1$ is an acid radical derived from sulfuric acid or orthophosphoric acid, and $m_1$ is 1 to 3 and $n_1$ is 4 to 40. Among these compounds, particularly interesting compounds are those of formula

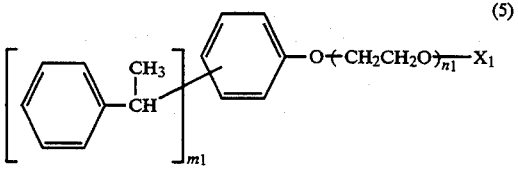

wherein $X_1$, $m_1$ and $n_1$ have the given meanings.

As anionic surfactants (b) in the novel formulations it is preferred to use component (bc), (bd) or (be).

The following compounds may be used as thickener (c):
(ca) ionically modified polysaccharides,
(cb) nonionic cellulose and derivatives thereof,
(cc) synthetic water-soluble carboxylates, or
(cd) polyvinyl alcohol,
(ce) bentonites, and
(cf) nonionic surfactants.

Component (ca) is selected from high molecular weight compounds which contain as basic component glucose, mannuronic acid, guluronic acid, mannose, galactose, xylose, arabinose, fucose, D-galactose or L-rhamnose. Both homo- as well as heteropolysaccharides are suitable, the homopolysaccharides being composed of homogeneous monosaccharide units, whereas the heteropolysaccharides may be composed of different basic components. Illustrative examples of anionic polysaccharides are carboxymethylated guar ethers, sodium carboxymethyl cellulose (Na-CMC), carboxymethyl starch, carboxymethylated carob bean gum and, most preferably, xanthane and sodium alginate.

Component (cb) is a nonionic cellulose derivative which is chemically modified, typically a cellulose ester or alkylated cellulose (cellulose ether), typically including methyl cellulose, hydroxyethyl cellulose, methylhydroxyethyl cellulose, hydroxypropyl cellulose and hydroxypropylmethyl cellulose.

Compounds suitable as component (cc) are primarily alkali metal salts of homo- or copolymers of acrylic acid with an average molecular weight of 100 000 to 300 000. Polyacrylic acid having a molecular weight of 150 000 to 200 000 is especially preferred.

The polyvinyl alcohol of component (cd) has a molecular weight of 15 000 to 1 500 000, preferably of 60 000 to 100 000, and a degree of hydrolysis of 80 to 100% molar, preferably of 85 to 90% molar.

Sparingly water-soluble nonionic surfactants suitable as component (cf) are:
(cfa) alkylene oxide polyadducts of
  (α) saturated or unsaturated mono- or hexahydric aliphatic alcohols,
  (β) fatty acids,
  (γ) fatty amines,
  (δ) fatty amides,
  (ε) diamines,
  (ζ) sorbitan esters,
(cfb) alkylene oxide condensates (block polymers),
(cfc) polymers of vinyl pyrrolidone, vinyl acetate or vinyl alcohol, and
(cfd) copolymers or terpolymers of vinyl pyrrolidone with vinyl acetate and/or vinyl alcohol.

The nonionic component (cfa) is conveniently
a polyadduct of alkylene oxide of 1 to 100 mol of alkylene oxide, conveniently ethylene oxide and/or propylene oxide, with 1 mol of an aliphatic monoalcohol containing at least 4 carbon atoms, of a trihydric to hexahydric aliphatic alcohol or of a phenol which may be substituted by alkyl, phenyl, α-tolylethyl, benzyl, α-methylbenzyl or αα-dimethylbenzyl;

a polyadduct of alkylene oxide of 1 to 1 00 mol, preferably 2 to 80 mol, of ethylene oxide with higher unsaturated or saturated monoalcohols (α), fatty acids (β), fatty amines (γ) or fatty amides (δ) of 8 to 22 carbon atoms, individual ethylene oxide units of which may be replaced by substituted epoxides such as styrene oxide and/or propylene oxide, a polyadduct of alkylene oxide, preferably of ethylene oxide and propylene oxide, with ethylenediamine (ε);

an ethoxylated sorbitan ester containing long chain ester groups, typically polyoxyethylene sorbitan monolaurate containing 4 to 20 ethylene oxide units, or polyoxyethylene sorbitan trioleate containing 4 to 20 ethylene oxide units (ζ).

Preferred components (cfb) are ethylene oxide/propylene adducts (EO-PO block polymers) and propylene oxide/polyethylene oxide adducts (reversed EO-PO block polymers).

Particularly preferred ethylene oxide/propylene oxide copolymers are those having molecular weights, based on polypropylene oxide, of 400 to 4000 and containing 30-80%, preferably 60-80%, of ethylene oxide in the entire molecule.

The thickener (c) of the novel formulations is preferably an ionically modified polysaccharide (component (ca)), more particularly sodium alginate or xanthane. Further important thickeners for the novel aqueous formulations are polyvinyl alcohols (component cd) with the molecular weights indicated above, as well as the nonionic surfactants of component (cf).

Important novel aqueous formulations comprise
(a) a colour former of formula (1), (b) an alkali metal salt of a sulfated ester of a $C_{10}$–$C_{18}$ fatty acid, and (c) an ionically modified polysaccharide.

Particularly important liquid formulations are those comprising
(a) a colour former of formula (1), wherein $R_2$ and $R_3$ are each independently of the other $C_1$–$C_4$alkyl,
(b) the sodium salt of a sulfated ester of a $C_{10}$–$C_{18}$ fatty acid, and
(c) sodium alginate.

Further interesting liquid formulations comprise
(a) a colour former of formula (1),
(b) an alkali metal salt of a sulfated ester of a $C_{10}$–$C_{18}$ fatty acid, and
(c) a sparingly water-soluble nonionic surfactant.

Further important novel formulations comprise
(a) a colour former of formula (1), wherein $R_2$ and $R_3$ are each independently of the other $C_1$–$C_4$alkyl,
(b) an anionic surfactant of formula (3), and
(c) sodium alginate.

The novel aqueous liquid formulations comprise, based on the weight of the entire formulation,
20 to 60% by weight, preferably 35 to 45% by weight, of a colour former (a)
1 to 15% by weight, preferably 3 to 8% by weight, of an anionic surfactant (b),
0.1 to 5% by weight, preferably 0.5 to 2% by weight, of a thickener (c), and water to make up 100%.

The preparation of the novel aqueous liquid formulations constitutes a further object of the invention. The process comprises milling the colour former (a) with the anionic surfactant (b) in the presence of water and then adding the thickener (c).

Milling is carded out in any type of mill, typically a glass bead mill, in the temperature range from 10° to 60° C., preferably from 15° to 20° C. The mixture of the colour former (a) and the anionic surfactant (b) is milled until a particle size of about 1 to 2 μm is obtained. Only then is the thickener stirred in. If desired, the novel formulations may contain microbicides. It is not necessary to add further ingredients such as antifoams to the novel aqueous liquid formulations.

The novel aqueous liquid formulations are highly concentrated aqueous mixtures which are easy to handle and have excellent storage properties.

The novel aqueous liquid formulations are used in heat-sensitive recording materials.

Thermoreactive recording systems typically comprise heat-sensitive recording or copying materials and papers. These systems are typically used for recording information, in electronic computers, printers, facsimile machines or copying machines or in medical and technical recording and measuring instruments. The image formation (marking) can also be effected manually with a heated stylus or a heated pen. Laser beams can also be used to produce heat-induced images.

The novel aqueous liquid formulation is stirred with a co-reactant to produce a coating composition. Suitable co-reactants are organic compounds containing a phenolic hydroxyl group. These compounds may be monohydric as well as polyhydric phenols. These phenols may be substituted by halogen atoms, carboxyl groups, alkyl radicals, acyl radicals such as arylsulfonyl, or alkoxycarbonyl radicals such as benzyloxycarbonyl.

Specific examples of suitable phenols are 4-tert-butylphenol, methylene bis(p-phenylphenol), 4-hydroxydiphenyl ether, α-naphthol, β-naphthol, methyl or benzyl 4-hydroxybenzoate, methyl 2,4-dihydroxybenzoate, 4-hydroxydiphenylsulfone, 4-hydroxy-4'-methyldiphenylsulfone, 4'-hydroxy-4-isopropoxydiphenylsulfone, 4-hydroxyacetophenone, 2,4-dihydroxybenzophenone, 2,2'-dihydroxydiphenyl, 2,4-dihydroxydiphenylsulfone, 4,4'-cyclohexylidenediphenol, 4,4'-isopropylidenediphenol, 4,4'-isopropylidene-bis(2-methylphenol), 4,4'-bis(hydroxyphenyl)valeric acid, resorcinol, hydroquinone, pyrogallol, phloroglucinol, p-, m- and o-hydroxybenzoic acid, 3,5-bis(α-methylbenzyl)salicylic acid, 3,5-bis(α,α-dimethylbenzyl)salicylic acid, salicylosalicylic acid, hydroxyphthalic acid, 1-hydroxy-2-naphthoic acid or phenol-formaldehyde prepolymers which may also be modified with zinc. Of the cited carboxylic acids, the salicylic acids are preferred and are preferably used as zinc salts. Especially preferred zinc salicylates are disclosed in EP-A-131 283 or DE-A-2 242 250. Particularly preferred co-reactants are zinc salicylates, metal-free phenols, phenolic resins or zinc-modified phenolic resins.

The formulation can be added to the appropriate coating composition using pumps, metering devices and applicator systems in accurately measured amounts.

The coating composition comprising the novel formulation and the co-reactants is applied with a suitable applicator system, conveniently a coating knife, as a thin layer to the thermoreactive recording material. The add-on is in the range from 0,1 to 1 g/m². The layer is softened or fused at specific areas by heat, such that the desired colour develops at once at the areas where heat is applied.

The thermoreactive layers may contain further auxiliaries. To improve the degree of whiteness, to facilitate the printing of papers, and to prevent the heated pen or plate from sticking, these layers may typically contain antioxidants, UV absorbers, solubilisers, talcum, titanium dioxide, zinc oxide, alumina, aluminium hydroxide, calcium carbonate (e.g. chalk), clays or also organic pigments, for example urea/formaldehyde polymers. To effect the colour formation only within a limited temperature range it is possible to add substances such as urea, thiourea, diphenyl thiourea, acetamide, acetanilide, benzene sulfanilide, bis(stearoyl)ethylenediamine, stearamide, phthalic anhydride, metal stearates such as zinc stearate, phthalonitrile, dimethyl terephthalate, dibenzyl terephthalate or other appropriate fusible products which induce the simultaneous melting of the colour former and the developer. Thermographic recording materials preferably contain waxes, including carnauba wax, montan wax, paraffin wax, polyethylene wax, condensates of higher fatty acid amides and formaldehyde, or condensates of higher fatty acids and ethylenediamine.

In the following working and application Examples parts and percentages are by weight.

Preparation of the liquid formulations

EXAMPLE 1

To 10 g (40%) of the colour former of formula

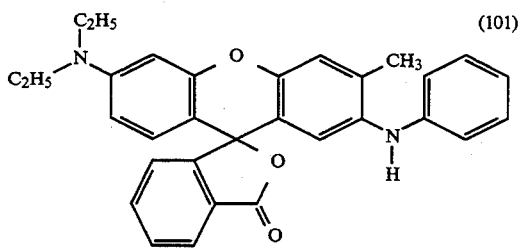
(101)

are added 1.25 g (5%) of the sodium salt of a monosulfosuccinate based on an ethoxylated alkanolamide and 13.5 g (54%) of water. In addition, 50 g of glass beads (diameter 1 mm) are added. The mixture is milled until the particle size is smaller than $2\mu$, preferably $1-1.5\mu$. The glass beads are then separated. Subsequently 0.25 g of gum arabic is added to the mixture as thickener.

EXAMPLE 2

To 10 g (40%) of the colour former of formula (101) are added 1.25 g (5%) of the sulfonated monoester of a $C_{12}-C_{22}$ fatty acid and 13.5 g (54%) of water, followed by the addition of 50 g of glass beads (diameter 1 mm). The mixture is milled until the particle size is smaller than $2\mu$, preferably $1-1.5\mu$. The glass beads are then separated. Subsequently 0.25 g (1%) of xanthane gum is added to the mixture as thickener.

EXAMPLE 3

To 10 g (40%) of the colour former of formula (101) are added 1.25 g (5%) of the sulfonated monoester of a $C_{12}-C_{22}$ fatty acid and 13.5 g (54%) of water, followed by the addition of 50 g of glass beads (diameter 1 mm). The mixture is milled until the particle size is smaller than $2\mu$, preferably $1-1.5\mu$. The glass beads are then separated. Subsequently 0.25 g (1%) of polyvinyl alcohol 100 000 is added to the mixture as thickener.

EXAMPLE 4

To 10 g (40%) of the colour former of formula (101) are added 1.25 g (5%) of the sulfonated monoester of a $C_{12}-C_{22}$ fatty acid and 13.5 g (54%) of water, followed by the addition of 50 g of glass beads (diameter 1 mm). The mixture is milled until the particle size is smaller than $2\mu$, preferably $1-1.5\mu$. The glass beads are then separated. Subsequently 0.25 g (1%) of sodium alginate is added to the mixture as thickener.

EXAMPLE 5

To 10 g (40%) of the colour former of formula (101) are added 1.25 g (5%) of the sulfonated monoester of a $C_{12}-C_{22}$ fatty acid and 13.625 g (54.5%) of water, followed by the addition of 50 g of glass beads (diameter 1 mm). The mixture is milled until the particle size is smaller than $2\mu$, preferably $1-1.5\mu$. The glass beads are then separated. Subsequently 0.125% (1%) of CMC (carboxymethyl cellulose) is added to the mixture as thickener.

EXAMPLE 6

To 10 g (40%) of the colour former of formula (101) are added 1.25 g (5%) of the sulfonated monoester of a $C_{12}-C_{22}$ fatty acid and 13.4625 g (53.85%) of water, followed by the addition of 50 g of glass beads (diameter 1 mm). The mixture is milled until the particle size is smaller than $2\mu$, preferably $1-1.5\mu$. The glass beads are then separated. Subsequently 0.25 g (1%) of NTC50 and 0.0375 g (0.15%) of xanthane gum are added to the mixture as thickeners.

EXAMPLE 7

To 10 g (40%) of the colour former of formula (101) are added 1.25 g (5%) of the sulfonated monoester of a $C_{12}-C_{22}$ fatty acid and 13.625 g (54.5%) of water, followed by the addition of 50 g of glass beads (diameter 1 mm). The mixture is milled until the particle size is smaller than $2\mu$, preferably $1-1.5\mu$. The glass beads are then separated. Subsequently 0.125% (0.5%) of κ-carageen is added to the mixture as thickener.

EXAMPLE 8

To 10 g (40%) of the colour former of formula (101) are added 1.25 g (5.%) of the sulfonated monoester of a $C_{12}-C_{22}$ fatty acid and 13.5 g (54%) of water, followed by the addition of 50 g of glass beads (diameter 1 mm). The mixture is milled until the particle size is smaller than $2\mu$, preferably $1-1.5\mu$. The glass beads are then separated. Subsequently 0.5 g (2%) of polyacrylic acid sodium salt 170 000 are added to the mixture as thickener.

EXAMPLE 9

To 10 g (40%) of the colour former of formula (101) are added 1.25 g (5%) of the sulfonated monoester of a $C_{12}-C_{22}$ fatty acid and 13.5 g (54%) of water, followed by the addition of 50 g of glass beads (diameter 1 mm). The mixture is milled until the particle size is smaller than $2\mu$, preferably $1-1.5\mu$. The glass beads are then separated. Subsequently 0.25% (1%) of bentonite is added to the mixture as thickener.

EXAMPLE 10

To 10 g (40%) of the colour former of formula (101) are added 1.25 g (5%) of the sodium salt of a monosulfosuccinate based oh an ethoxylated alkanolamide and 13.69 g (54.75%) of water, followed by the addition of 50 g of glass beads (diameter 1 mm). The mixture is milled until the particle size is smaller than $2\mu$, preferably $1-1.5\mu$. The glass beads are then separated. Subsequently 0.063 g (0.25%) of an ethylene oxide/propylene oxide copolymer with a molecular weight of c. 2000 is added to the mixture as thickener.

EXAMPLE 11

To 10 g (40%) of the colour former of formula (101) are added 1.25 g (5%) of the sodium salt of a monosulfosuccinate based on an ethoxylated alkanolamide and 12.5 g (50%) of water, followed by the addition of 50 g of glass beads (diameter 1 mm). The mixture is milled until the particle size is smaller than $2\mu$, preferably $1-1.5\mu$. The glass beads are then separated. Subsequently 1.25 g (5%) of the polyadduct of 1 mol of a $C_{13}$oxoalcohol and 3 mol of ethylene oxide are added to the mixture as thickener.

EXAMPLE 12

To 10 g (40%) of the colour former of formula (101) are added 1.25 g (5%) of the anionic surfactant of formula

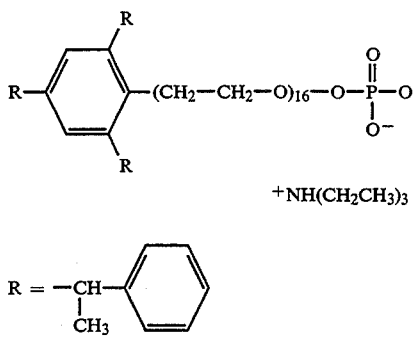

(102)

R = —CH—C₆H₅
     |
     CH₃ and 12.5 g (50%) of water, followed by the addition of 50 g of glass beads (diameter 1 mm). The mixture is milled until the particle size is smaller than 2 g, preferably 1–1.5μ. The glass beads are then separated. Subsequently 0.25 g (1%) of sodium alginate is added to the mixture as thickener.

EXAMPLE 13

The procedure of Example 12 is repeated, but replacing 0.25 g of sodium alginate with 0.25 g (1%) of bentonite as thickener.

EXAMPLE 14

Instead of the colour former of formula (101) in Examples 1 to 13 it is also possible to use the colour former of formula

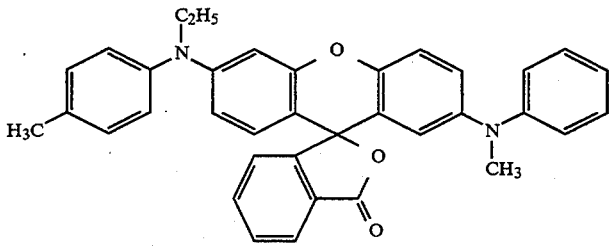

(103)

EXAMPLE 15

Instead of the colour former of formula (101) in Examples 1 to 13 it is also possible to use the colour former of formula

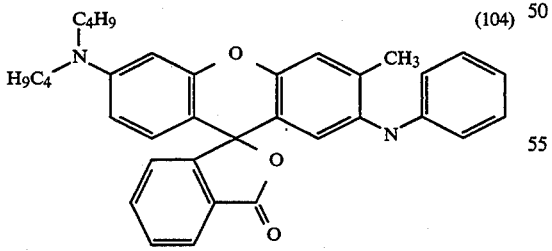

(104)

Application Examples

EXAMPLE 16

0.6 g of the liquid formulation prepared according to Example 1 is mixed with 13.38 g of a co-reactant mixture comprising
3.8% of biphenyl and
3.0% of benzyl diphenyl and the composition is applied with a coating knife to a paper to a weight per unit area of 0.5 g/m². When the paper is used in a facsimile machine (Infotec, supplied by CANON), a deep, lightfast black copy is obtained.

EXAMPLES 17-23

The liquid formulation prepared according to Example 1 is replaced with the liquid formulations prepared according to Examples 2-16 and the procedure described in Example 16 is carried out. Deep, lightfast black copies are also obtained.

What is claimed is:

1. A concentrated liquid formulation of a colour former comprising a) 20 to 60 percent by weight of color former which is a fluoran compound of formula

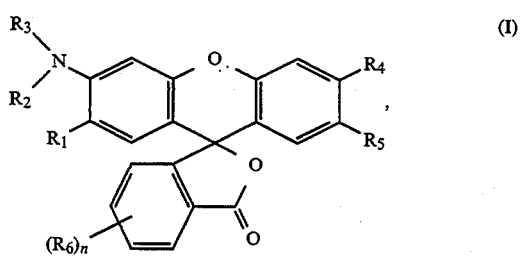

(I)

wherein
$R_1$ is hydrogen or $C_1$–$C_4$alkyl;
$R_2$ and $R_3$ are each independently of the other hydrogen; $C_1$–$C_{12}$alkyl; unsubstituted or $C_1$–$C_4$alkyl- or halogen-substituted $C_4$–$C_7$cycloalkyl; unsubstituted phenyl or phenyl which is substituted by $C_1$–$C_4$alkyl, hydroxy or halogen; phenyl-$C_1$–$C_4$alkyl; $C_3$–$C_6$alkenyl; $C_1$–$C_4$alkoxy; $C_1$–$C_4$alkoxy-$C_1$–$C_4$alkyl; 2-tetrahydrofuranyl, or
$R_2$ and $R_3$ together with the linking nitrogen atom are an unsubstituted or $C_1$–$C_4$alkyl-substituted pyrrolidino, piperidino, morpholino, thiomorpholino or piperazino ring;
$R_4$ is hydrogen, hydroxy or $C_1$–$C_4$alkyl;
$R_5$ is nitro; $SO_2R_7$; $SO_2OR_8$; $SO_2NR_9R_{10}$; $COR_{11}$; $CONR_9R_{10}$; $C_1$–$C_4$haloalkyl; $C_6$–$C_{10}$aryl which is unsubstituted or substituted by halogen, $C_1$–$C_4$alkyl, $C_1$–$C_4$haloalkyl, $C_1$–$C_4$alkoxy; phenylamino; phenyl-$C_1$–$C_4$alkylamino; phenyl-$C_1$–$C_4$alkyl; an unsubstituted or a halogen- or hydroxy-substituted 2-triazinyl or 1-benzotriazolyl radical;
$R_6$ is halogen; nitro; $C_1$–$C_4$alkyl; $C_1$–$C_4$haloalkyl; amino; mono-$C_1$–$C_4$alkylamino; di-$C_1$–$C_4$alkylamino; or $COR_{11}$;
n is 0; 1; 2; 3; or 4;

R$_7$ is C$_1$–C$_8$alkyl; or C$_1$–C$_8$haloalkyl; unsubstituted phenyl or phenyl-C$_1$–C$_4$alkyl or phenyl or phenyl-C$_1$–C$_4$alkyl which are substituted by halogen, C$_1$–C$_4$alkyl, C$_1$–C$_4$haloalkyl or C$_1$–C$_4$alkoxy;

R$_8$ is hydrogen, C$_1$–C$_8$alkyl; C$_1$–C$_8$haloalkyl; unsubstituted phenyl or phenyl-C$_1$–C$_4$alkyl or phenyl or phenyl-C$_1$–C$_4$alkyl which are substituted by halogen, C$_1$–C$_4$alkyl, C$_1$–C$_4$haloalkyl, C$_1$–C$_4$alkoxy;

R$_9$ and R$_{10}$ are each independently of the other hydrogen; or C$_1$–C$_8$alkyl; or R$_9$ and R$_{10}$, together with the linking nitrogen atom, are an unsubstituted or a C$_1$–C$_4$alkyl-substituted pyrrolidino, piperidino, morpholino, thiomorpholino or piperazino ring; and R$_{11}$ is hydrogen; hydroxy; C$_1$–C$_8$ alkyl; C$_1$–C$_8$alkoxy; C$_1$–C$_8$haloalkyl; unsubstituted phenyl or phenyl which is substituted by halogen, C$_1$–C$_4$alkyl, C$_1$–C$_4$haloalkyl, or C$_1$–C$_4$alkoxy; phenyl-C$_1$–C$_4$alkyl or phenyl-C$_1$–C$_4$alkoxy;

(b) 1 to 15 percent by weight of an anionic surfactant selected from the group consisting of
(ba) sulfated alkanes,
(bb) alkanesulfonates,
(bc) sulfonated carboxylates,
(bd) sulfated carboxylates, and
(be) acid esters or salts thereof of polyadducts of alkylene oxides, (c) 0.1 to 5 percent by weight of a thickener, and water to make 100 percent.

2. A liquid formulation according to claim 1, wherein the colour former is a fluoran of formula (1), wherein
R$_1$ is hydrogen or C$_1$–C$_4$alkyl;
R$_2$ and R$_3$ are each independently of the other hydrogen; C$_1$–C$_5$ alkyl; or
R$_2$ and R$_3$, together with the linking nitrogen atom, are an unsubstituted or C$_1$–C$_4$alkyl-substituted pyrrolidino or piperidino ring;
R$_4$ is hydrogen or C$_1$–C$_4$alkyl;
R$_5$ is nitro; SO$_2$R$_7$; SO$_2$OR$_8$; SO$_2$NR$_9$R$_{10}$; COR$_{11}$; CONR$_9$R$_{10}$; C$_1$–C$_4$haloalkyl; unsubstituted phenyl or phenyl which is substituted by halogen, C$_1$–C$_4$alkyl, C$_1$–C$_4$haloalkyl, C$_1$–C$_4$alkoxy; phenylamino; or phenyl-C$_1$–C$_4$alkylamino;
n is 0; 1; 2; 3; or 4;
R$_6$ if n is 1, 2, 3, or 4, is halogen; if n is 1 or 2, is C$_1$–C$_4$alkyl, C$_1$–C$_4$haloalkyl; or, if n is 1, is nitro, COR$_{11}$, amino, mono-C$_1$–C$_4$alkylamino or di-C$_1$–C$_4$alkylamino;
R$_7$ is C$_1$–C$_4$alkyl; or C$_1$–C$_4$haloalkyl; unsubstituted phenyl or phenyl-C$_1$–C$_2$alkyl o phenyl or phenyl-C$_1$–C$_2$alkyl which are substituted by halogen, C$_1$–C$_4$alkyl, C$_1$–C$_4$haloalkyl or C$_1$–C$_4$alkoxy;
R$_8$ is hydrogen, C$_1$–C$_4$alkyl; C$_1$–C$_4$haloalkyl; unsubstituted phenyl or phenyl-C$_1$–C$_2$alkyl or phenyl or phenyl-C$_1$–C$_2$alkyl which is substituted by halogen, C$_1$–C$_4$alkyl, C$_1$–C$_4$haloalkyl, C$_1$–C$_4$alkoxy;
R$_9$ and R$_{10}$ are each independently of the other hydrogen; or C$_1$–C$_8$ alkyl; or
R$_9$ and R$_{10}$ together with the linking nitrogen atom are an unsubstituted or a C$_1$–C$_4$alkyl-substituted pyrrolidino or piperidino ring; and
R$_{11}$ is hydrogen; C$_1$–C$_4$alkyl; C$_1$–C$_4$haloalkyl; C$_1$–C$_4$alkoxy; unsubstituted phenyl or phenyl which is substituted by halogen, C$_1$–C$_4$alkyl, C$_1$–C$_4$haloalkyl, or C$_1$–C$_4$alkoxy; or is phenyl-C$_1$–C$_2$alkyl or phenyl-C$_1$–C$_2$alkoxy.

3. A liquid formulation according to claim 1, wherein the colour former is a fluoran of formula (1), wherein
R$_1$ is hydrogen or methyl;
R$_2$ and R$_3$ are each independently of the other hydrogen; C$_1$–C$_5$alkyl; or
R$_2$ and R$_3$, together with the linking nitrogen atom, are an unsubstituted pyrrolidino or piperidino ring;
R$_4$ is hydrogen or methyl;
R$_5$ is nitro; SO$_2$R$_7$; SO$_2$NR$_9$R$_{10}$; COR$_{11}$; CONR$_9$R$_{10}$; C$_1$–C$_4$haloalkyl; unsubstituted phenyl or phenyl which is substituted by halogen, C$_1$–C$_4$alkyl, C$_1$–C$_4$haloalkyl, C$_1$–C$_4$alkoxy; or is phenyl-C$_1$–C$_4$alkyl; phenylamino; or phenyl-C$_1$–C$_4$alkylamino;
n is 0, 1, 2, 3, or 4;
R$_6$ if n is 1, 2, 3, or 4, is halogen; if n is 1 or 2, is methyl; or, if n is 1, is nitro, amino, mono-C$_1$–C$_4$alkylamino or di-C$_1$–C$_4$alkylamino;
R$_7$ is C$_1$–C$_4$alkyl; or C$_1$–C$_4$haloalkyl; unsubstituted phenyl or phenyl which is substituted by halogen, C$_1$–C$_4$alkyl, or C$_1$–C$_4$alkoxy;
R$_9$ and R$_{10}$ are each independently of the other hydrogen; or C$_1$–C$_4$alkyl;
R$_{11}$ is hydrogen; C$_1$–C$_4$alkyl; C$_1$–C$_4$alkoxy; unsubstituted phenyl or phenyl which is substituted by halogen, C$_1$–C$_4$alkyl, C$_1$–C$_4$haloalkyl, or C$_1$–C$_4$alkoxy; or is phenyl-C$_1$–C$_2$alkyl or phenyl-C$_1$–C$_2$alkoxy.

4. A liquid formulation according to claim 1, comprising at least one colour former of formula (I), wherein R$_5$ is COR$_{11}$.

5. A liquid formulation according to claim 4, wherein R$_{11}$ is C$_1$–C$_4$alkyl, C$_1$–C$_4$alkoxy or phenyl-C$_1$–C$_4$alkoxy.

6. A liquid formulation according to claim 1, comprising at least one colour former of formula (I), wherein R$_5$ is phenyl; phenylamino; or phenyl-C$_1$–C$_4$alkylamino.

7. A liquid formulation according to claim 1, wherein the colour former is a fluoran of formula (1), wherein R$_2$ and R$_3$ are each independently of the other C$_1$–C$_4$alkyl.

8. A liquid formulation according to any claim 1, wherein the anionic surfactant (ba) is a salt of fatty alcohol sulfates of formula

wherein R$_{12}$ is an alkyl radical of 6 to 18 carbon atoms, and M$_1$ is alkali metal.

9. A liquid formulation according to claim 1, wherein the anionic surfactant (bb) is a secondary alkanesulfonate having an alkyl chain length of 14 to 18 carbon atoms.

10. A liquid formulation according to claim 1, wherein the anionic surfactant (bc) is a compound of formula

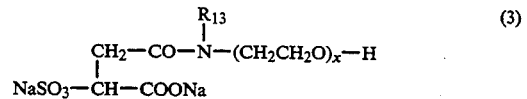

wherein
R$_{13}$ is hydrogen or (CH$_2$CH$_2$O)$_x$H and x is 1 to 10.

11. A liquid formulation according to claim 1, wherein the anionic surfactant (bd) is selected from the group consisting of alkali metal salts, ammonium salts or amine salts of sulfated esters of fatty acids of 10 to 22 carbon atoms.

12. A liquid formulation according to claim 1, wherein the anionic surfactant (be) is a compound of formula

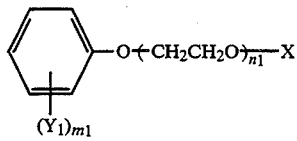

(4)

wherein $Y_1$ is $C_4$–$C_{12}$alkyl, phenyl, tolyl, phenyl-$C_1$–$C_3$alkyl or tolyl-$C_1$–$C_3$alkyl, $X_1$ is an acid radical derived from sulfuric acid or orthophosphoric acid, and $m_1$ is 1 to 3 and $n_1$ is 4 to 40.

13. A liquid formulation according to claim 12, wherein the anionic surfactant (be) is a compound of formula

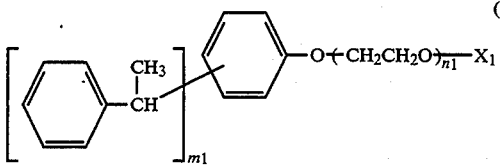

(5)

wherein $X_1$ is an acid radical which is derived from sulfuric acid or orthophosphoric acid, $m_1$ is 1 to 3, and $n_1$ is 4 to 40.

14. A liquid formulation according to claim 1, wherein the thickener is selected from the group consisting of:
(ca) ionically modified polysaccharides,
(cb) nonionic cellulose and derivatives thereof,
(cc) synthetic water-soluble carboxylates,
(cd) polyvinyl alcohol,
(ce) bentonites, and
(cf) nonionic surfactants.

15. A liquid formulation according to claim 14, wherein the thickener is an ionically modified polysaccharide.

16. A liquid formulation according to claim 14, wherein the thickener is sodium alginate.

17. A liquid formulation according to claim 14, wherein the thickener is xanthane.

18. A liquid formulation according to claim 14, wherein component (cc) is polyacrylic acid having a molecular weight of 150 000 to 200 000.

19. A liquid formulation according to claim 14, wherein the thickener is a polyvinyl alcohol having a molecular weight of 15 000 to 1 500 000.

20. A liquid formulation according to claim 14, wherein the nonionic surfactant (cf) is a copolymer of ethylene oxide and propylene oxide.

21. A liquid formulation according to claim 14, wherein the nonionic surfactant (cf) is a polyadduct of alkylene oxide with saturated or unsaturated monohydric to hexahydric aliphatic alcohols.

22. A liquid formulation according to claim 1, comprising
(a) a colour former of formula (1),
(b) an alkali metal salt of a sulfated ester of a $C_{10}$–$C_{18}$fatty acid, and
(c) an ionically modified polysaccharide.

23. A liquid formulation according to claim 22, comprising
(a) a colour former of formula (1), wherein $R_2$ and $R_3$ are each independently of the other $C_1$–$C_4$alkyl, and $R_5$ is phenyl; phenylamino; or phenyl-$C_1$–$C_4$alkylamino,
(b) the sodium salt of a sulfated ester of a $C_{10}$–$C_{18}$fatty acid, and
(c) sodium alginate.

24. A liquid formulation according to claim 22, comprising
(a) a colour former of formula (1), wherein $R_2$ and $R_3$ are each independently of the other $C_1$–$C_4$alkyl, and $R_5$ is phenyl; phenylamino; or phenyl-$C_1$–$C_4$alkylamino,
(b) an anionic surfactant of formula (3), and
(c) sodium alginate.

25. A liquid formulation according to claim 1, comprising
(a) a colour former of formula (1),
(b) an alkali metal salt of a sulfated ester of a $C_{10}$–$C_{18}$fatty acid, and
(c) a sparingly water-soluble nonionic surfactant.

26. A process for the preparation of a liquid formulation as claimed in claim 1, which comprises milling the colour former (a) with the anionic surfactant (b) in the presence of water and then adding the thickener (c).

27. A liquid formulation according to claim 1, wherein the color former is a fluoran of formula (1), wherein $R_2$ and $R_3$ are independently of each other hydrogen, $C_1$–$C_5$alkyl, $C_5$–$C_7$cycloalkyl, benzyl or allyl.

* * * * *